(12) United States Patent
Diguet et al.

(10) Patent No.: US 8,211,471 B2
(45) Date of Patent: Jul. 3, 2012

(54) PROCESS FOR THE PRODUCTION OF BEADLETS

(75) Inventors: Sylvain Diguet, Hagenthal-le-haut (FR); Torsten Huber, Magden (CH); Johann Ulm, Oberwil (CH)

(73) Assignee: DSM IP Assets B.V., Heerlen (NL)

( * ) Notice: Subject to any disclaimer, the term of this patent is extended or adjusted under 35 U.S.C. 154(b) by 105 days.

(21) Appl. No.: 12/416,638

(22) Filed: Apr. 1, 2009

(65) Prior Publication Data

US 2009/0214661 A1 Aug. 27, 2009

Related U.S. Application Data

(62) Division of application No. 10/542,049, filed as application No. PCT/EP2004/002821 on Mar. 18, 2004, now abandoned.

(30) Foreign Application Priority Data

Mar. 27, 2003 (EP) .................................. 03007009

(51) Int. Cl.
*A61K 9/14* (2006.01)
*A23L 1/30* (2006.01)
*A23B 4/16* (2006.01)
*A01N 31/04* (2006.01)

(52) U.S. Cl. .......... 424/489; 424/484; 426/73; 426/311; 426/312; 514/725

(58) Field of Classification Search ........... None
See application file for complete search history.

(56) References Cited

U.S. PATENT DOCUMENTS

| | | | |
|---|---|---|---|
| 4,670,247 A * | 6/1987 | Scialpi | 424/484 |
| 5,043,170 A | 8/1991 | Borenstein et al. | |
| 5,126,328 A | 6/1992 | Bower et al. | |
| 5,356,636 A | 10/1994 | Schneider et al. | |
| 5,364,563 A | 11/1994 | Cathrein et al. | |
| 5,487,916 A | 1/1996 | Christensen | |
| 5,668,183 A | 9/1997 | Leuenberger | |
| 5,811,609 A | 9/1998 | Vilstrup et al. | |
| 6,328,995 B1 | 12/2001 | Bewert et al. | |
| 6,413,548 B1 | 7/2002 | Hamer et al. | |
| 6,444,227 B1 * | 9/2002 | Leuenberger et al. | 424/489 |

FOREIGN PATENT DOCUMENTS

| | | |
|---|---|---|
| EP | 0 261 616 | 3/1988 |
| EP | 0 285 682 | 10/1988 |
| EP | 0 494 417 | 7/1992 |
| EP | 0 633 058 | 1/1995 |
| EP | 0 807 431 | 11/1997 |
| EP | 0 982 038 | 3/2000 |
| EP | 1 074 592 | 2/2001 |
| FR | 2 243 727 | 4/1975 |
| GB | 993138 | 5/1965 |
| WO | WO 91/17821 | 11/1991 |
| WO | 01/91576 | 12/2001 |
| WO | WO 03/017785 | 3/2003 |

OTHER PUBLICATIONS

Cortesi et al, "Sugar cross-linked gelatin for controlled release: microspheres and disks", Biomaterials, Elsevier Science Publishers BV, Parking, GB, vol. 19, No. 18, Sep. 1998, pp. 1641-1649.
International Search Report, dated Aug. 28, 2004 (filed with U.S. Appl. No. 10/542,049).
Remington: The Science and Practice of Pharmacy (19$^{th}$ Ed.), vol. II, (1995); p. 1414.
"Dictionary of Pharmaceutical Additive 2007," Yakuji Nippo Limited, 2007 First Edition, pp. 96, 97, 155.

* cited by examiner

Primary Examiner — Robert A Wax
Assistant Examiner — Jeffrey T Palenik
(74) Attorney, Agent, or Firm — Nixon & Vanderhye P.C.

(57) ABSTRACT

A process for the production of cross-linked beadlets containing one or more active ingredients selected from the group of a fat-soluble vitamin active material, a carotenoid and a polyunsaturated fatty acid is provided. The process comprises treating a dry particulate form at a temperature in the range of from 90° C. to 140° C. for a time period of from 30 seconds to 30 minutes or from 1 minute to 10 minutes or from 3 minutes to 7 minutes.

8 Claims, No Drawings

PROCESS FOR THE PRODUCTION OF BEADLETS

CROSS-REFERENCE TO RELATED APPLICATIONS

This application is a divisional of commonly owned U.S. application Ser. No. 10/542,049, filed on Jul. 13, 2005 now abandoned, which is the national phase application under 35 USC §371 of PCT/EP2004/002821 filed Mar. 18, 2004, and claims the benefit of priority from EP 03007009.8 filed Mar. 27, 2003, the entire content of each being hereby incorporated by reference.

FIELD OF THE INVENTION

The present invention relates to a process for the production of beadlets with a high concentration of an active ingredient selected from a fat soluble vitamin, a carotenoid and a polyunsaturated fatty acid, to the resulting beadlets and to compositions containing them.

BACKGROUND OF THE INVENTION

The prior art discloses fat-soluble vitamin powder compositions which are useful for administration as such and also for the formation of pharmaceutical dosage forms, for example, tablets, capsules, powders, and the like; and for the preparation of animal feeds.

U.S. Pat. No. 2,756,177 discloses a process for preparing dry, free-flowing powders by forming an emulsion containing a vitamin-active material, water, gelatin, and/or gum acacia and a sugar; converting the emulsions to droplets; collecting the individual droplets in a mass of starchy powder in such a manner that the vitamin-active particles formed from the droplets are kept separated from each other until their particulate form is established; and separating the vitamin-active particles from the starchy collecting powder. The vitamin-containing powder prepared according to the above process is water soluble and exhibits satisfactory stability properties for most uses; however, the material does have problems withstanding the stresses of pelletizing when used for the fortification of animal feeds. The vitamin containing material tends to lose its physical integrity under the temperature, moisture, and pressure conditions of the feed pelleting process and results in a loss of the physical integrity of the product thereby compromising the stability of the fat-soluble vitamin.

U.S. Pat. No. 4,670,247 relates to a vitamin-active preparation in the form of a water insoluble beadlet comprising the steps of forming an emulsion containing the vitamin-active material, water, gelatin, and a sugar; converting the emulsion to droplets; collecting the individual droplets in a mass of starchy powder in such a manner that the vitamin-active particles from the droplets are kept separated from each other until their particulate is permanently established; separating the vitamin-active particles from the starchy collecting powder, and heat treating the particles at a temperature of from about 90° C. to about 180° C. In accordance with this process, the heat treatment step insolubilizes the gelatin matrix of the beadlet by a reaction between the carbonyl group of the sugar with the free amino moieties of the gelatin molecule. The resulting beadlets are water-insoluble and exhibit increased stability to the stresses of feed pelleting. The crosslinking process utilizes the ingredients employed in making the beadlet and does not require addition of a crosslinking reagent or additive to the composition.

SUMMARY OF THE INVENTION

Starting from U.S. Pat. No. 4,670,247 it is an important object of the invention to provide a vitamin-active preparation in the form of beadlets not only characterized by high stability and potency but also characterized with an increased concentration of the active ingredient. A further object is to provide a vitamin-active beadlet with a reduced loss of active ingredients in the surface region.

More particularly the invention provides a process for the production of cross-linked beadlets containing one or more active ingredients selected from the group of a fat-soluble vitamin active material, a carotenoid and a polyunsaturated fatty acid, the process comprising treating a dry particulate form at a temperature in the range of from 90° C. to 140° C. for a time period of from 30 seconds to 30 minutes or from 1 minute to 10 minutes or from 3 minutes to 7 minutes.

DETAILED DESCRIPTION

Examples of a fat-soluble vitamin active material include vitamin bearing oils, provitamins and pure or substantially pure vitamins, both natural and synthetic, or chemical derivatives thereof and mixtures thereof. Of particular interest is a vitamin selected from the group of vitamins A, D, E and K, and derivatives thereof. For example, the term "Vitamin E" includes synthetically manufactured tocopherols or a mixture of natural tocopherols. Examples of vitamin derivatives include vitamin A acetate, vitamin A palmitate and vitamin E acetate. An example for a vitamin D-active material is vitamin $D_3$. As a particular example, the process of the present invention may result in a beadlet containing a vitamin A-active material and a vitamin D-active material, e.g. vitamin A and vitamin $D_3$.

In one embodiment the process of the invention may involve Vitamin A as fat-soluble vitamin active material in a total concentration in the range of from 500,000 IU vitamin A/g beadlet to 1,500,000 IU vitamin A/g beadlet, in the range of from 750,000 IU vitamin A/g beadlet to 1,500,000 IU vitamin A/g beadlet, or in the range of from 750,000 IU vitamin A/g beadlet to 1,300,000 IU vitamin A/g beadlet, e.g. vitamin A may be present in the beadlet in a total concentration of 500,000±35,000 IU active ingredient/g beadlet, 750,000±35,000 IU active ingredient/g beadlet, of 1,000,000±35,000 IU active ingredient/g beadlet, or of 1,100,000±35,000 IU active ingredient/g beadlet. Vitamin D as fat-soluble vitamin active material may be present in the range of from 100,000 IU vitamin D/g beadlet to 500,000 IU vitamin D/g beadlet or in the range of from 100,000 IU vitamin D/g beadlet to 200,000 IU vitamin D/g beadlet, vitamin E as fat-soluble vitamin active material may be present in the range of from 50% to 75% vitamin E.

Examples for a carotenoid include β-carotene, lycopene, zeaxanthin, astaxanthin, lutein, capsanthin and cryptoxanthin.

In one embodiment the process of the invention may involve a carotenoid in a total concentration in the range of from 5% to 20%, in the range of from 5% to 15%, or in the range of from 7% to 15%.

Examples for a polyunsaturated fatty acid, as triglyceride and/or ethylester, include arachidonic acid, eicosapentaenoic acid, docosahexaenoic acid and γ-linolenic acid and/or ethyl ester.

In one embodiment the process of the invention may involve a polyunsaturated fatty acid as triglyceride in a total concentration in the range of from 20% to 50%, in the range of from 25% to 40%, or in the range of from 28% to 38%.

The dry particulate forms used in the process of the present invention may be prepared by any procedure known to the skilled artisan, e.g. by forming an aqueous emulsion containing the active ingredient, an emulsifier, a texturing agent and a reducing sugar, followed by converting the emulsion to a dry particulate form containing the non-aqueous constituents of said emulsion.

Examples for an emulsifier are gelatine and ascorbyl palmitate. Gelatine is an emulsifier which at the same time functions as a texturing agent. Any gelatine which has a "bloom" in the range of practically zero to about 300 can be employed in the practice of the present invention. Both Type A and Type B gelatine can be employed. The preferred gelatine used is Bloom 140, but gelatine Bloom 30 or Bloom 75 would be possible as well. In the presence of gelatine no additional texturing agent may be necessary.

The concentration of the emulsifier depends on the kind of emulsifier used, e.g. gelatine may be present in a concentration in the range of from 25% to 35%, or less.

Examples for a texturing agent beyond gelatine include carrageenan, modified starch, modified cellulose, xanthan gum, acacia gum, pectins, guar, caroub gums, maltodextrines and alginates.

The concentration of the texturing agent depends on the kind of texturing agent used and may be, e.g., in the range of from 0% to 15%.

Examples for a reducing sugar are fructose, glucose, lactose, maltose, xylose, arabinose, ribose and sucrose. One type of sugar may be used or a mixture of two or more sugars. The reducing sugar may be added as such or in the form of a syrup, e.g. fructose or glucose syrup.

The concentration of the reducing sugar depends on the kind of reducing sugar used and may be, e.g., in the range of from 2% to 10%, or in a ratio of gelatine:sugar in the range of from 3:1 to 7:1, e.g. 5:1.

Small quantities of other ingredients may be incorporated including antioxidants like 6-ethoxy-1,2-dihydroxy-2,2,4-trimethylquinoline (ethoxyquine), 3,5-di-tertiary-4-butyl hydroxytoluene (BHT) and 3-tertiary butyl-hydroxyanisole (BHA), humectants such as glycerol, sorbitol, polyethylene glycol, propylene glycol, extenders and solubilizers.

As a typical example gelatine and a suitable sugar may be dissolved in water previously mixed with glycerin. The dissolution may last at 65-70° C. for, e.g., about 30 minutes. Then, e.g., the vitamin A with the antioxidant may be added and emulsified. The pre-emulsification may be done with a colloid mill, e.g., based on a rotor/stator principle. The pre-emulsification may be hold for between 15 and 30 minutes at a rotation speed of the rotor between 500 and 1500 rpm and may then pass through a high pressure homogeniser resulting in a conversion of the emulsion to fine droplets.

In one example the conversion of emulsion droplets to "set up" particles may be attained by introducing a spray of emulsion droplets into an agitated cloud or suspension in air of the particles of the finely dispersed powder, e.g. by forcing the emulsion through a revolving spray head into a suspension in air of the powdered material, contained in and agitated by a revolving cylindrical drum, the drum and the spray head rotating in opposite directions so that the cloud or suspension of the powder in air is swirling in a sense of rotation opposite to the entering emulsion spray.

Examples of the finely dispersed powder used in the process to collect/coat the droplets of the emulsion include polysaccharides such as starch and modified starch, and calcium silicate alone or a mixture of calcium silicate with one of the following mixture components: microcrystalline cellulose, magnesium silicate, magnesium oxide, stearic acid, calcium stearate, magnesium stearate, hydrophilic silicic acid and kaolin. Coatings which consist of calcium silicate alone are preferred. The calcium silicate may be present wholly or partially in the form of the hydrate.

The calcium silicate particles are especially suitable when they have a size of less than 0.2 μm, especially less than 0.1 μm, and a specific surface of at least about 80 m$^2$/g to about 180 m$^2$/g, preferably of about 95 m$^2$/g to 120 m$^2$/g, and are agglomerated to aggregates having an average size of about 5-30 μm, preferably 5-20 μm. The SiO$_2$/CaO ratio lies between 1.65 and 2.65.

In coatings which consist of calcium silicate alone, the amount of calcium silicate may be in the range of from 2 wt. % to 12 wt. %, preferably in the range of from 4 wt. % to 9 wt. %.

In coatings consisting of a mixture of calcium silicate with one or more of the aforementioned mixture components, the amount of the calcium silicate mixture may be in the range of from 5 wt. % to 25 wt. %.

Optionally, the resulting dry particulate forms may be separated from the remaining finely dispersed powder. This may be accomplished by operations which are conventional per se, including, e.g. simply to feed the mixture of powder and dry particulate forms to a shaking screen of a size selected to retain the dry particulate forms while passing the collecting powder.

For further processing those dry particulate forms containing the active material are preferred having a moisture content of less than 10% and preferably between about 4 to 6 percent. If the moisture content is higher the dry particulate forms may be dried to the desired moisture content by various methods, e.g. by exposing them to air at room temperature or by moderate heating in a drying oven at 37° C. to 45° C.

The heat treatment may, e.g., be achieved in a batch or in a continuous process where the beadlet residence time and temperature are controlled.

In the case of a fluid bed process, the beadlet is added either at the beginning in the case of the batch process or constantly in the case of a continuous fluid bed in a hot air or nitrogen stream having a temperature between 100 and 200° C., preferably between 130-160° C. The beadlet temperature is raised in a few second to one minute above 100° C. enabling a quick and efficient reaction. The beadlet is ready after 5 to 10 minutes. The beadlet is cooled at the end of the treatment.

In the case of a continuous flash treatment, the beadlet is fed continuously into a hot gas stream having a temperature between 100 and 200° C., preferably between 130-160° C. The beadlet can be moved by mechanical stirring, e.g., above 300 rpm. The wall of the vessel used to make this thermal treatment can also be heated to a temperature in the range of from 110 to 180° C. The desired crosslinking of the beadlet may be reached in a time in the range of from 30 seconds to 10 minutes or from 1 minute to 10 minutes, with a maximum beadlet temperature in the range of from 90° C. to 140° C., preferably from 105° C. to 125° C.

The beadlet forms resulting from the inventive process have a core and a surface region, wherein the loss of active ingredients in the surface region is reduced, and are also an object of the present invention.

Therefore, the present invention further provides a beadlet form having a core and a surface region, wherein the core region contains, in a high concentration, one or more active ingredients selected from the group of a fat-soluble vitamin active material, a carotenoid and a polyunsaturated fatty acid, and the surface region contains less than 10% of the total active ingredient content, preferably less than 5% of the total active ingredient content.

In one embodiment the present invention provides a beadlet form containing one or more active ingredients selected from the group of Vitamin A in a total concentration in the range of from 800,000 IU vitamin A/g beadlet to 1,500,000 IU vitamin A/g beadlet or in the range of from 950,000 IU vitamin A/g beadlet to 1,250,000 IU vitamin A/g beadlet, in a total concentration in the range of from 100,000 IU vitamin D/g beadlet to 500,000 IU vitamin D/g beadlet or in the range of from 100,000 IU vitamin D/g beadlet to 200,000 IU vitamin D/g beadlet, vitamin E in a total concentration in the range of from 50% to 75%, a carotenoid in a total concentration in the range of from 5 to 20% and a polyunsaturated fatty acid in a total concentration in the range of from 5 to 50%, wherein the surface region contains less than 10% of the total active ingredient content. In another embodiment the surface region contains less than 5% of the total active ingredient content.

The beadlets are characterized by high stability and potency. They exhibit high stability when pelletized, e.g. they withstand the temperature, moisture and pressure of a feed pelleting process without losing their physical integrity. They are water insoluble and maintain their properties in relation to bioavailability.

Typical examples of beadlets of the present invention may, e.g. have the following components: 30% to 45% of vitamin A, 0% to 2% of vitamin $D_3$, 5% to 15% of 6-ethoxy-1,2-dihydro-2,2,4-trimethylquinoline (EMQ), 25% to 35% of gelatine, 5% to 10% of fructose, 2% to 10% of glycerine, 5% to 10% of calcium silicate, 0% to 25% of corn starch, 0% to 1% of edible fat, and water.

EXAMPLE 1

Preparation of Beadlets Containing 1,000,000 IU Vitamin A/g Beadlet Plus 200,000 IU Vitamin $D_3$/g Beadlet Approximately 90 parts of gelatine Bloom 140 and 18 parts of fructose were dissolved in 313.2 parts of water (containing 23.2 parts of glycerin) by heating at 65° C. 158 parts of Vitamin A containing 24% ethoxyquin (assay 2.1 Mio. IU vitamin A per g) and 3.5 parts of vitamin $D_3$ (assay 20 Mio. IU vitamin $D_3$ per g) were then mixed with the resulting matrix, followed by pre-emulsification.

The beadlet was sprayed using as finely dispersed powder calcium silicate. The average particle size of the beadlet was in the range of from 200 µm to 300 µm.

The beadlet was divided into two groups: one group was treated using a classical heated slow mixer without sufficient control of the thermal history of the beadlet, and the other group was treated by a fluidized bed, i.e. a batch process with an apparatus where the temperature and residence time of the beadlet can be controlled. The results are compared in the following table:

|  | heated slow mixer | fluidized bed |
|---|---|---|
| Vitamin A content after crosslinking (IU/g) | 1,025,000 | 1,050,000 |
| Vitamin A Loss (%) | 3-4 | 0-1 |
| Surface vitamin A (%) | 8-10 | 1-2 |
| Crosslinking grade (%) | 76% | 82% |

In the fluidized bed the temperature was controlled between 100 and 115° C. for 5 minutes. In the heated slow mixer, the beadlet was heated for about 15 minutes at a temperature raising from 90° C. to 124° C.

EXAMPLE 2

Preparation of Beadlets Containing 1,000,000 IU Vitamin A/g Beadlet

Approximately 100 parts of gelatine Bloom 140 and 20 parts of fructose were dissolved in 308.2 parts of water (containing 13.2 parts of glycerin) by heating at 65° C. 170 parts of Vitamin A containing 24% ethoxyquin (assay 2.1 Mio. IU vitamin A per g) were then mixed with the resulting matrix, followed by pre-emulsification.

The beadlet was sprayed using as finely dispersed powder calcium silicate. The average particle size of the beadlet was in the range of from 180 µm to 270 µm.

The beadlet was divided into three groups: the first group was treated using a classical heated slow mixer as in Example 1, the second group was treated by a fluidized bed as in Example 1, the third group was treated by a continuous flash treatment in diluted phase wherein the flash treatment is ensured by a combination of pneumatic transport and mechanical transport. The results are compared in the following table:

|  | heated slow mixer | fluidized bed | flash treatment |
|---|---|---|---|
| Vitamin A content after crosslinking (IU/g) | 1,119,000 | 1,146,000 | 1,143,000 |
| Vitamin A Loss (%) | 3-4 | 0-1 | 0-1 |
| Surface vitamin A (%) | 8-10 | 2-2.5 | 3-5 |
| Crosslinking grade (%) | 50-80 | 50-80 | 50-80 |

In the fluidized bed the temperature was controlled between 110 and 120° C. for 5 minutes. In the flash treatment, the beadlet was treated for 1 to 4 minutes at a temperature raising from 115° C. to 125° C. In the heated slow mixer, the beadlet was heated for about 20 minutes at a temperature raising from 70° C. to 124° C.

EXAMPLE 3

Stability of Beadlets Containing a High Concentration of Vitamin A

Typical stability performance in terms of retention time after a storage time of 4 weeks at 40° C. and 75% rH for the cross-linked beadlets of Example 1 and Example 2 are about 90-95% which is comparable to standard cross-linked vitamin A forms containing 500'00 IU vitamin A/g active ingredient.

EXAMPLE 4

Preparation of Beadlets Containing 1,000,000 IU Vitamin A/g Beadlet

Approximately 100 parts of gelatine Bloom 140 and 20 parts of fructose were dissolved in 308.2 parts of water (containing 13.2 parts of glycerin) by heating at 65° C. 170 parts of Vitamin A containing 24% ethoxyquin (assay 2.1 Mio. IU vitamin A per g) were then mixed with the resulting matrix, followed by pre-emulsification.

The beadlet was sprayed using as finely dispersed powder calcium silicate. The average particle size of the beadlet was in the range of from 200 µm to 300 µm.

The beadlets of 3 lots were treated by a continuous flash treatment in diluted phase wherein the flash treatment is ensured by a combination of pneumatic transport and mechanical transport. The results are compared in the following table:

|  | Lot 1 | Lot 2 | Lot 3 |
|---|---|---|---|
| Vitamin A content after crosslinking (IU/g) | 1'064'808 | 1'051'641 | 1'077'224 |
| Vitamin A Loss (%) | <1 | <1 | <1 |
| Surface vitamin A (%) | 3.7 | 4.0 | 3.5 |
| Crosslinking grade (%) | 60-85 | 60-85 | 60-85 |

In the flash treatment, the beadlet was treated for 1 to 5 minutes at a temperature raising from 105° C. to 115° C.

EXAMPLE 5

Stability of Beadlets Containing a High Concentration of Vitamin A

Typical stability performances in terms of retention time after a storage time of 4 weeks at 40° C. and 75% rH for the cross-linked beadlets of Example 4 are about 95-100% which are comparable to standard cross-linked vitamin A forms containing 500'00 IU vitamin A/g active ingredient.

EXAMPLE 6

Preparation of Beadlets Containing 1,000,000 IU Vitamin A/g Beadlet Plus 200,000 IU Vitamin $D_3$/g Beadlet Approximately 90 parts of gelatine Bloom 140 and 18 parts of fructose were dissolved in 313.2 parts of water (containing 23.2 parts of glycerin) by heating at 65° C. 158 parts of Vitamin A containing 24% ethoxyquin (assay 2.1 Mio. IU vitamin A per g) and 3.5 parts of vitamin $D_3$ (assay 20 Mio. IU vitamin $D_3$ per g) were then mixed with the resulting matrix, followed by pre-emulsification.

The beadlet was sprayed using as finely dispersed powder calcium silicate. The average particle size of the beadlet was in the range of from 200 μm to 300 μm.

The beadlets of 3 lots were treated by a continuous flash treatment in diluted phase wherein the flash treatment is ensured by a combination of pneumatic transport and mechanical transport. The results are compared in the following table:

|  | Lot 1 | Lot 2 | Lot 3 |
|---|---|---|---|
| Vitamin A content after crosslinking (IU/g) | 1'105'039 | 1'074'633 | 1'077'470 |
| Vitamin D3 content after crosslinking (IU/g) | 218'617 | 214'813 | 217'858 |
| Vitamin A Loss (%) | <1 | <1 | <1 |
| Surface vitamin A (%) | 4.7 | 4.7 | 4.6 |
| Crosslinking grade (%) | 60-85 | 60-85 | 60-85 |

In the flash treatment, the beadlet was treated for 1 to 5 minutes at a temperature raising from 105° C. to 115° C.

EXAMPLE 7

Stability of Beadlets Containing a High Concentration of Vitamin A and D3

Typical stability performances in terms of retention time after a storage time of 4 weeks at 40° C. and 75% rH for the cross-linked beadlets of Example 6 are about 95-100% and about 100% for vitamin A and D3 respectively, which are comparable to standard cross-linked vitamin AD3 forms containing 500'00 IU vitamin A/g and 100'000 IU vitamin D3/g active ingredient.

The invention claimed is:

1. A process for the production of cross-linked beadlets containing vitamin A which comprises the steps of:
    (a) forming an emulsion containing vitamin A, an emulsifier and a reducing sugar,
    (b) converting the emulsion to droplets,
    (c) coating the droplets with finely dispersed calcium silicate powder,
    (d) separating a dry particulate form of beadlets obtained by step (c) from remaining finely dispersed calcium silicate powder, and
    (e) heat treating the dry particulate form of beadlets to obtain a maximum beadlet temperature in the range of from 90° C. to 140° C. within a time period of from 30 seconds to 30 minutes to thereby form a final beadlet having a total vitamin A concentration of from 800,000 IU vitamin A/g beadlet to 1,500,000 IU vitamin A/g beadlet with a core and a surface region, wherein the surface region contains less than 10% of the total vitamin A concentration of the final beadlet.

2. The process according to claim 1, wherein the dry particulate form has a moisture content of less than 10%.

3. The process according to claim 1, wherein the heat treatment of step (e) is practiced as a batch or a continuous process wherein beadlet residence time and temperature are controlled.

4. The process according to claim 1, wherein the heat treatment of step (e) comprises introducing the beadlet to a hot air or nitrogen stream having a temperature between 100 and 200° C. to obtain the maximum beadlet temperature.

5. The process according to claim 1, wherein the heat treatment of step (e) is practiced by raising the temperature of the dry particulate form of the beadlets to above 100° C. within a time ranging from a few seconds to 1 minute.

6. The process according to claim 1, wherein the heat treatment of step (e) is practiced to achieve a maximum beadlet temperature in the range of from 110° C. to 140° C.

7. The process according to claim 1, wherein the time period for heating treating the dry particulate form of beadlets according to heat treatment of step (e) is from 1 minute to 10 minutes.

8. The process according to claim 1, wherein the time period for heating treating the dry particulate form of beadlets according to the heat treatment of step (e) is from 3 minutes to 7 minutes.

* * * * *